United States Patent
Honda

(10) Patent No.: US 8,077,144 B2
(45) Date of Patent: Dec. 13, 2011

(54) MEDICAL IMAGE DISPLAY APPARATUS

(75) Inventor: Takemitsu Honda, Tokyo (JP)

(73) Assignee: Olympus Corporation, Tokyo (JP)

( * ) Notice: Subject to any disclaimer, the term of this patent is extended or adjusted under 35 U.S.C. 154(b) by 1110 days.

(21) Appl. No.: 11/864,060

(22) Filed: Sep. 28, 2007

(65) Prior Publication Data

US 2008/0084428 A1    Apr. 10, 2008

(51) Int. Cl.
 *G09G 5/00* (2006.01)
(52) U.S. Cl. .......................... 345/156; 345/160
(58) Field of Classification Search ........... 345/156–173
 See application file for complete search history.

(56) References Cited

U.S. PATENT DOCUMENTS

| | | | |
|---|---|---|---|
| 6,856,315 B2* | 2/2005 | Eberlein | 345/440 |
| 7,801,351 B2* | 9/2010 | Srinivas et al. | 382/132 |
| 2002/0030682 A1* | 3/2002 | Eberlein | 345/440 |
| 2002/0154140 A1* | 10/2002 | Tazaki | 345/620 |
| 2003/0090498 A1* | 5/2003 | Schick et al. | 345/661 |
| 2004/0066389 A1* | 4/2004 | Skyba et al. | 345/619 |
| 2005/0184958 A1* | 8/2005 | Gnanamgari et al. | 345/157 |
| 2006/0061595 A1* | 3/2006 | Goede et al. | 345/619 |
| 2007/0126730 A1* | 6/2007 | Goto et al. | 345/418 |

FOREIGN PATENT DOCUMENTS

| | | |
|---|---|---|
| JP | 10-333871 | 12/1998 |
| JP | 11-032304 | 2/1999 |
| JP | 2001-14016 | 1/2001 |
| JP | 2002-290783 | 10/2002 |
| JP | 2002-351293 | 12/2002 |
| JP | 2003-019111 | 1/2003 |
| JP | 2003-346172 | 12/2003 |
| JP | 2004-321603 | 11/2004 |
| JP | 2004-337596 | 12/2004 |
| JP | 2005-33484 | 2/2005 |

OTHER PUBLICATIONS

Japanese Office Action dated May 11, 2010 together with Partial Translation.

* cited by examiner

*Primary Examiner* — Nitin Patel
(74) *Attorney, Agent, or Firm* — Scully, Scott, Murphy & Presser, P.C.

(57) ABSTRACT

Provided is an image display apparatus which includes a display unit that displays a series of images obtained by imaging an inside of a subject in time sequence, and displays a specific area with a predetermined size; and an input unit having an input button group for performing a display operation of the images. The apparatus also includes a control unit that performs a control so that an operation mode is set to a button operation mode for performing the display operation of the images with a button operation of the input unit when a cursor on a display screen is in the specific area, and the operation mode is set to a cursor operation mode for performing the display operation of the images corresponding to at least a position on the display screen and a position of the cursor when the cursor is out of the specific area.

9 Claims, 11 Drawing Sheets

MEDICAL IMAGE DISPLAY APPARATUS

BACKGROUND OF THE INVENTION

1. Field of the Invention

The present invention relates to an image display apparatus that displays a series of images obtained by imaging a subject in time sequence.

2. Description of the Related Art

Recently, a swallowable capsule endoscope provided with an imaging function and a radio communication function has been proposed in an endoscope field, and a capsule endoscope system for acquiring an image in a subject with the use of the capsule endoscope has been developed. The capsule endoscope moves in a body cavity, for example, inside of internal organs such as stomach, small intestine, etc., due to peristaltic movement, and functions to capture an image inside the subject at an interval of 0.5 second, during the period from when it is swallowed from a mouth of the subject for observation (examination) to when it is naturally discharged.

While the capsule endoscope moves in the subject, the image captured by the capsule endoscope is transmitted sequentially to an external receiving apparatus via radio communication. The receiving apparatus has a radio communication function and a memory function. It sequentially stores the image of the inside of the subject received from the capsule endoscope into a memory. By carrying the receiving apparatus, the subject can freely move during the period from when he/she swallows the capsule endoscope to when it is naturally discharged. After the capsule endoscope is naturally discharged from the subject, a doctor or nurse causes an image display apparatus to read the image accumulated in the memory for displaying the image of the internal organs in the subject by the image display apparatus, whereby the doctor or nurse can perform diagnosis of the subject (for example, see Japanese Patent Application Laid-Open No. 2003-19111).

The image display apparatus described above generally displays each image contained in a series of images of the inside of the subject as a still image, or displays each image consecutively to display a pseudo-moving image of the inside of the subject. There is one of such image display apparatuses having a moving image display function described above in which, in order to perform a display operation of a moving image on a screen, a slider that is a rectangle display area and a knob moving in the slider are displayed on a screen, and the knob is moved by a drag operation with the use of a mouse to carry out a display operation of a moving image (see, for example, Japanese Patent Application Laid-Open No. 11-32304). In the image display apparatus disclosed in Japanese Patent Application Laid-Open No. 11-32304, an origin is provided in the vicinity of the center of the slider on the screen, and when the knob is moved so as to be apart from the origin, the moving image is displayed with a reproduction speed according to the position of the knob. On the other hand, there is an image display apparatus that displays icon formed with plural button sections for operating a moving direction and moving speed of an image, and has a function of moving the image on a screen in a desired direction by selecting any one of button sections of the icon with the movement of the mouse and performing a click operation (see, for example, Japanese Patent Application Laid-Open No. 2003-346172).

However, whenever a desired image group, e.g., a series of images in the subject, is displayed with its play speed and play direction (specifically, forward direction or reverse direction in the time sequence) changed to the desired play speed and play direction, a display operation for moving the mouse should be performed, i.e., a cursor on the screen should be moved to the icon, etc., to perform a click operation or drag operation in the conventional image display apparatus. Therefore, there has been a problem that it is in many cases difficult to perform the display operation of the image while observing a series of images in the subject.

SUMMARY OF THE INVENTION

An image display apparatus according to an aspect of the present invention includes a display unit that displays a series of images obtained by imaging an inside of a subject in time sequence, and displays a specific area with a predetermined size; an input unit having an input button group for performing a display operation of the images; and a control unit that performs a control so that an operation mode is set to a button operation mode for performing the display operation of the images with a button operation of the input unit when a cursor on a display screen is in the specific area, and the operation mode is set to a cursor operation mode for performing the display operation of the images corresponding to at least a position on the display screen and a position of the cursor when the cursor is out of the specific area.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, a preferred embodiment of an image display apparatus of the present invention is described in detail. Although, in the following, an image display apparatus used in a capsule endoscope system is exemplified as an example of the image display apparatus of the present invention, this does not limit the scope of the present invention.

Figure 1:
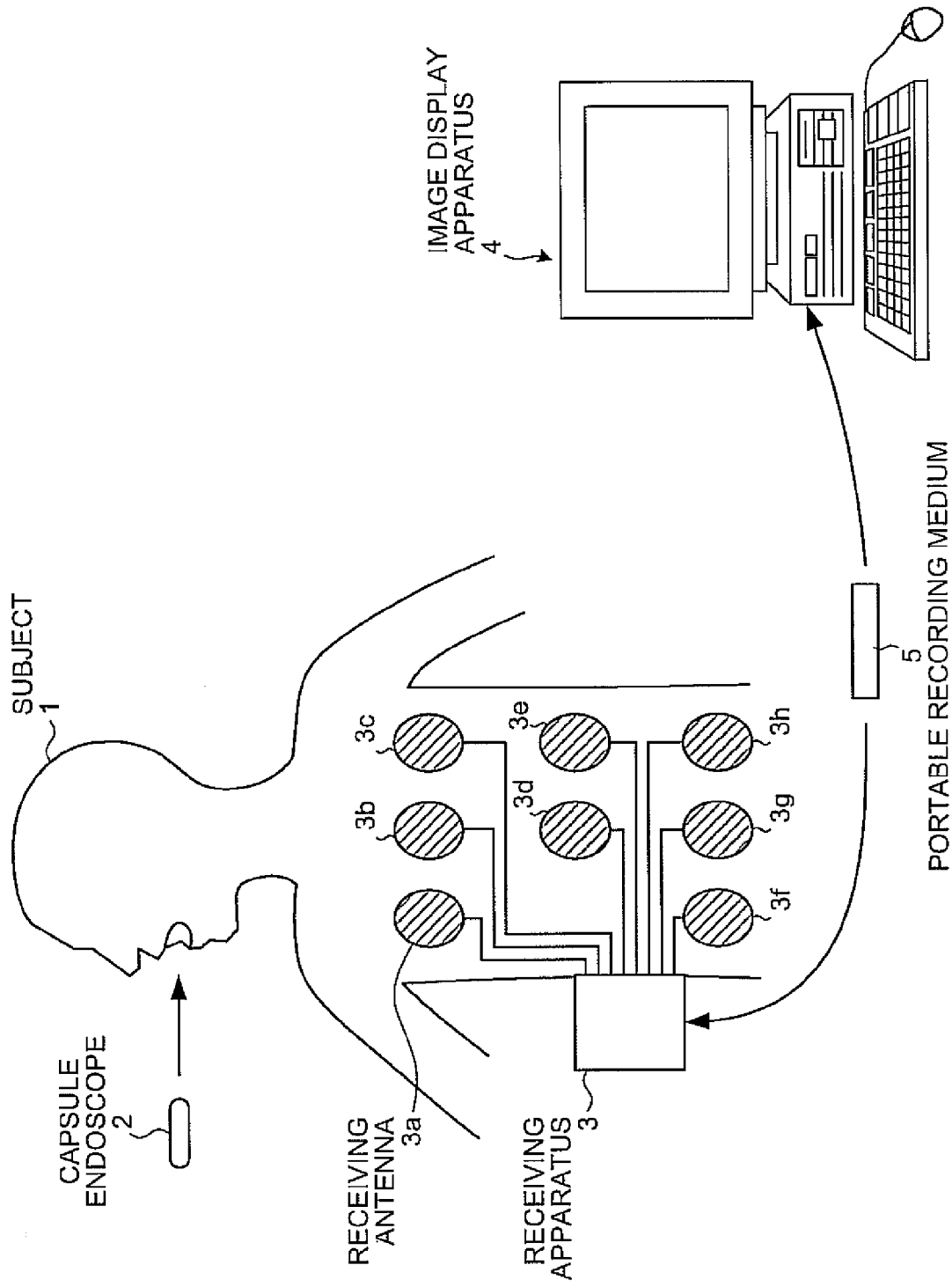
FIG. 1 is a schematic diagram schematically illustrating one example of a configuration of a capsule endoscope system provided with an image display apparatus according to one embodiment of the present invention.

FIG. 1 is a schematic view schematically illustrating one structural example of a capsule endoscope system provided with an image display apparatus according to an embodiment of the present invention. As shown in FIG. 1, this capsule endoscope system has a capsule endoscope 2 that moves along a moving path in a subject 1 so as to captures an image in the subject 1, a receiving apparatus 3 that receives the image radio-transmitted from the capsule endoscope 2 and accumulates the image, an image display apparatus 4 that displays the image obtained by imaging the subject 1 by the capsule endoscope 2 in time sequence, and a portable recording medium 5 that receives and transmits information between the receiving apparatus 3 and the image display apparatus 4.

The capsule endoscope 2 has a imaging function for imaging the inside of the subject 1 and a radio communication function for transmitting the image of the inside of the subject 1 to the receiving apparatus 3. The capsule endoscope 2 is swallowed by the subject 1, so that it passes an esophagus in the subject 1, and advances in a body cavity due to peristalsis of a cavity of an alimentary tract. Simultaneously, the capsule endoscope 2 sequentially captures an image in the subject 1 at a predetermined interval, for example, at an interval of 0.5 second, and sequentially transmits the obtained image in the subject 1 to the receiving apparatus 3.

The receiving apparatus 3 has connected thereto receiving antennas 3a to 3h so as to perform radio communication with the capsule endoscope 2 with the use of the receiving antennas 3a to 3h. Specifically, the receiving apparatus 3 receives a radio signal from the capsule endoscope 2 via any one of the receiving antennas 3a to 3h, and acquires the image in the subject 1 on the basis of the received radio signal. Further, the portable recording medium 5 is detachably mounted to the receiving apparatus 3, wherein the image in the subject 1 sequentially acquired from the capsule endoscope 2 is sequentially stored in the portable recording medium 5.

The receiving antennas 3a to 3h are realized by using, for example, a loop antenna, and receive radio signals transmitted from the capsule endoscope 2. The receiving antennas 3a to 3h are arranged at a predetermined position on the body surface of the subject 1, e.g., the position corresponding to the moving path of the capsule endoscope 2, as shown in FIG. 1. The receiving antennas 3a to 3h may be arranged at the predetermined position on a jacket put on the subject 1. In this case, since the subject 1 wears this jacket, the receiving antennas 3a to 3h are arranged at the predetermined position on the body surface of the subject 1 corresponding to the moving path of the capsule endoscope 2. It may suffice that plural receiving antennas are arranged on the subject 1. In this case, the number of the arranged antennas is not particularly limited to eight.

The portable recording medium 5 is a portable recording media such as CompactFlash®, etc. The portable recording medium 5 is attachable to and detachable from the receiving apparatus 3 and the image display apparatus 4, and has a structure capable of outputting and recording information upon being attached to both apparatuses. Specifically, when the portable recording medium 5 is attached to the receiving apparatus 3, the receiving apparatus 3 sequentially stores data such as the image, etc. obtained from the capsule endoscope 2. When the portable recording medium 5 is attached to the image display apparatus 4, the stored data such as the image etc. is taken into the image display apparatus 4, or information relating to the subject 1 is written by the image display apparatus 4.

The image display apparatus 4 displays the image, etc. captured by the capsule endoscope 2. The image display apparatus 4 has a configuration like a workstation, or the like, so as to display the image in the subject 1 obtained through the portable recording medium 5. In this case, the image display apparatus 4 has a processing function by which an examiner such as a doctor or a nurse observes the image of the inside of the subject 1 and diagnoses the subject 1. The examiner causes the image display apparatus 4 to sequentially display the image in the subject 1 for observing (examining) the sites in the subject 1, such as an esophagus, stomach, small intestine, large intestine, etc., whereby the examiner can diagnose the subject 1.

Figure 2:
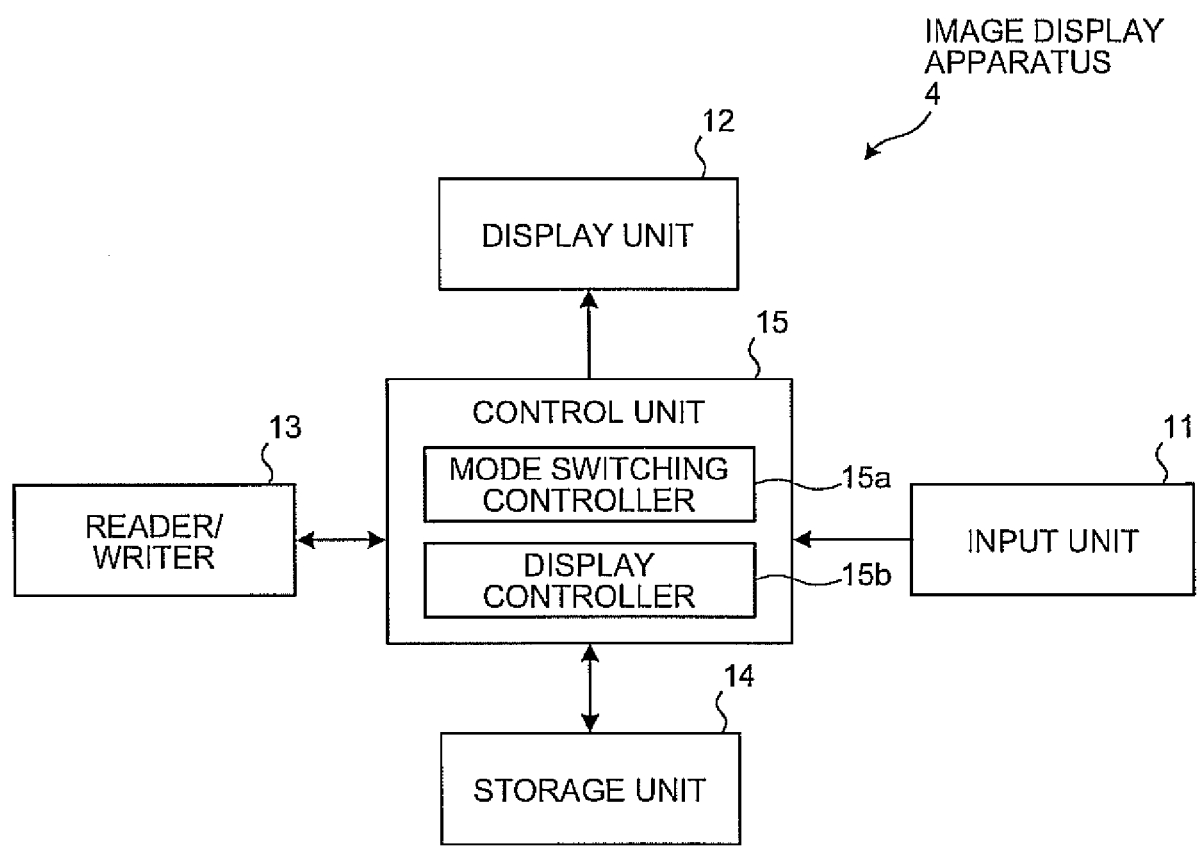
FIG. 2 is a block diagram schematically showing one example of the configuration of the image display apparatus according to the embodiment of the present invention.

FIG. 2 is a block diagram schematically showing one structural example of the image display apparatus 4. As shown in FIG. 2, the image display apparatus 4 has an input unit 11 that inputs various information so as to display and observe the image in the subject 1, a display unit 12 that displays on a screen various information pieces for observing (examining) the inside of the subject 1 such as the image of the inside of the subject 1 for diagnosis, and a reader/writer 13 that takes data such as an image or the like accumulated in the portable recording medium 5. Further, the image display apparatus 4 has a storage unit 14 that accumulates various data pieces necessary for the observation and diagnosis of the inside of the subject 1 such as the image of the inside of the subject 1, and a control unit 15 that drives and controls various units in the image display apparatus 4.

The input unit 11 is realized by using a ten-key, keyboard, mouse, and the like. The input unit 11 inputs information giving an instruction to the control unit 15 or information relating to the subject 1 to the control unit 15 through the input operation by the examiner. Further, the input unit 11 has an input button group for performing a display operation for displaying a desired image group, e.g., a series of images in the subject 1, on the display unit 12 with a desired play speed (i.e., display frame rate) along the forward direction or reverse direction of the time sequence. In this case, the input unit 11 inputs to the control unit 15 instruction information for displaying the image in the subject 1 on the display unit 12 and information relating to the subject 1, such as a name of the subject 1 (patient name), sex, birth date, and patient ID.

The display unit 12 is realized by using a display such as a CRT display or liquid crystal display, and displays various information pieces instructed to display by the control unit 15. In this case, the display unit 12 displays, for example, a series of images in the subject 1 captured by the capsule endoscope 2 with the desired play speed along the forward direction or reverse direction of the time sequence. The specific example of the display screen by the display unit 12 will be described later.

The above-mentioned portable recording medium 5 is detachably mounted to the reader/writer 13. The reader/writer 13 takes the data, e.g., a series of images in the subject 1, accumulated in the mounted portable recording medium 5, and transfers the obtained data to the control unit 15. Further, the reader/writer 13 writes the information instructed to be written by the control unit 15, e.g., the information relating to the subject 1, to the mounted portable recording medium 5.

The storage unit 14 accumulates the information instructed to be written by the control unit 15, e.g., a series of images in the subject 1 and the information relating to the subject 1. Further, the storage unit 14 reads the accumulated information, which is instructed by the control unit 15 to be read, and transfers the same to the control unit 15. It is to be noted that the storage unit 14 may be configured to accumulate various information pieces into the storage unit 14 itself by using information recording means capable of accumulating and reading the information, such as RAM, EEPROM, hard disk, or the like, or alternatively, the storage unit 14 may be configured such that a portable recording medium such as CD or DVD is detachably mounted thereto and information is accumulated into the mounted CD or DVD.

The control unit 15 drives and controls each unit of the image display apparatus 4, such as the input unit 11, display unit 12, reader/writer 13, and storage unit 14, as described above, and performs input/output control of the information to each unit and information processing for inputting and outputting various information pieces between each unit. When the control unit 15 takes, for example, a series of images in the subject 1 through the portable recording medium 5, the control unit 15 associates and stores each image of the series of images and time information relating to each image into the storage unit 14.

The control unit 15 further has a mode switching controller 15a and a display controller 15b. The mode switching controller 15a performs a control so as to change a display operation mode for displaying the series of images in the subject 1 on the display unit 12. In this case, the mode switching controller 15a changes the display operation mode to either one of a button operation mode and cursor operation mode according to the position of the cursor on the display screen of the display unit 12. The mode switching controller 15a performs a control to change a display operation state of the image displayed on the display unit 12, corresponding to the display operation using the input unit 11. In this case, the mode switching controller 15a mode-shifts the display operation state of the image to the next display operation state for every display operation using the input unit 11.

The cursor operation mode performs the display operation of the image corresponding at least to the position on the display screen and the position of the cursor, e.g., the cursor operation mode is the display operation mode for changing the display operation state of the image according to any one of the display operation icon groups formed on the display screen and the position of the cursor (specifically, the cursor is moved to any one of the display operation icon groups). On the other hand, the button operation mode performs the display operation of the image by the button operation of the input unit 11. For example, the button operation mode is the display operation mode for changing the display operation state of the image by the button operation of, for example, the mouse or keyboard, without moving the cursor to any one of the display operation icon groups.

The above-mentioned image display operation state is the state of the image on the display screen classified depending upon the play speed and play direction (i.e., in the forward direction or reverse direction of the time sequence). Examples of the image display state include a state in which the image display is temporarily stopped (pause state), a state in which an image is displayed with a reference play speed in the forward direction of the time sequence (play state), a state in which an image is displayed with a play speed, which is higher than the reference play speed, in the forward direction of the time sequence (fast play state), and a state in which an image is displayed with frame feeding along the forward direction of the time sequence (frame play state). Further, examples of the image display operation state includes a state in which an image is displayed with the play direction of the play state changed to the reverse direction of the time sequence (reverse play state), a state in which an image is displayed with the play direction of the fast play state changed to the reverse direction of the time sequence (reverse fast play state), and a state in which an image is displayed with the play direction of the frame play state changed to the reverse direction of the time sequence (reverse frame play state).

On the other hand, the display controller 15b performs a control to display various information pieces to the display unit 12. In this case, the display controller 15b causes the display unit 12 to display the information for observing and diagnosing the inside of the subject 1, such as the series of the image of the inside of the subject 1. Further, the display controller 15b performs a control to display on the display unit 12 a guidance image that explains for the examiner the button operation for changing the above-mentioned image display operation state (specifically, for mode-shifting to the next display operation state) in the button operation mode. The detail of the guidance image will be described later.

Figure 3:
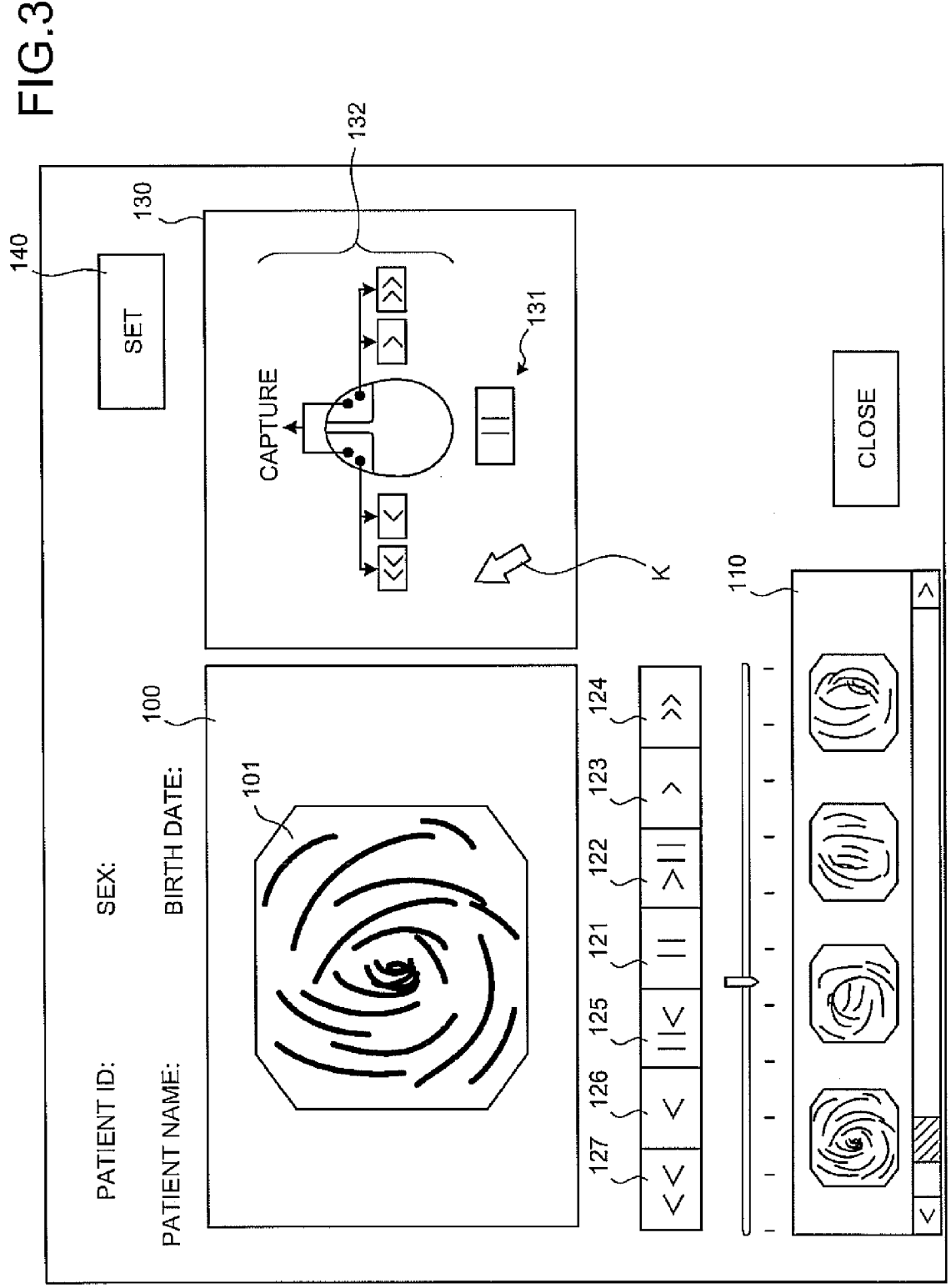
FIG. 3 is a schematic view schematically showing one specific example of a display screen.

Subsequently, the display screen displayed by the display unit 12 will be specifically explained. FIG. 3 is a schematic view schematically showing one specific example of the display screen of the display unit 12. As shown in FIG. 3, formed on the display screen of the display unit 12 are a main-image display area 100 that displays an observation image by which an examiner observes (examines) the inside of the subject, a subimage display area 110 that additionally displays a desired image selected from the images displayed on the main-image display area 100 as a thumbnail, and display operation icons 121 to 127 for performing the image display operation displayed on the main-image display area 100 in the above-mentioned cursor operation mode. Further, formed on the display screen of the display unit 12 are a cursor K that moves on the display screen by the operation of the input unit 11, a specific area 130 that is formed into a size by which the cursor K can go in or out, and a setting icon 140 that performs a user setting to select the input unit 11 used for the image display operation.

As shown in FIG. 3, an observation image 101 for observing (examining) the inside of the subject 1 is displayed on the main-image display area 100. The observation image 101 is included in the series of images in the subject 1 captured by the capsule endoscope 2, and is displayed with the display operation state designated by the display operation of the input unit 11.

Every time the examiner operates the input unit 11 to select the desired image in the main-image display area 100, the thumbnail corresponding to the selected desired image is additionally displayed on the subimage display area 110. When the observation image 101 in the main-image display area 100 is selected, for example, the thumbnail corresponding to the observation image 101 is additionally displayed on the subimage display area 110.

The display operation icons 121 to 127 are for performing the display operation of the image displayed in the main-image display area 100 in the aforesaid cursor operation mode. Specifically, in the cursor operation mode, the cursor K is moved to any one of the display operation icons 121 to 127, and the display operation icon at the position of the cursor K is selected by the operation of the input unit 11, whereby the display operation state of the observation image displayed in the main-image display area 100 is designated. In this case, the observation image is displayed in the main-image display area 100 with the display operation state corresponding to the display operation icon thus designated.

The display operation icon 121 designates the pause state of the observation image in the cursor operation mode, and the display operation icons 122 to 124 respectively designate the frame play state, play state, and fast play state of the observation image in the cursor operation mode. Further, the display operation icons 125 to 127 respectively designate the reverse frame play state, reverse play state, and reverse fast play state in the cursor operation mode.

The specific area 130 is the area formed into the size by which the cursor K can go in the frame or out of the frame as shown in FIG. 3. The specific area 130 is formed, for example, in the vicinity of the main-image display area 100. Further, a state image 131 and a guidance image 132 are displayed in the specific area 130. The state image 131 is for showing the display operation state of the image, which is being displayed in the main-image display area 100, to the examiner. Specifically, the state image 131 is displayed so as to indicate the mark of the display operation icon (for example, any one of the display operation icons 121 to 127) designating the display operation state same as the present display operation state, in order to show the display operation state of the image that is being displayed in the main-image display area 100. In this case, when the image now being displayed, for example, the observation image 101 is in the pause state, the state image 131 is displayed so as to indicate the mark "| |" of the display operation icon 121 designating the pause state.

The guidance image 132 is, as described above, for explaining to the examiner the button operation of the input unit 11 in order to change the image display operation state (i.e., to mode-shift to the next display operation state) in the button operation mode. When a user setting for selecting the mouse as the input unit 11 used for the image display operation is performed beforehand, for example, the guidance image 132 explains the button operation of the mouse for mode-shifting the current display operation state (e.g., pause state) to the next display operation state as shown in FIG. 3.

Figure 4:
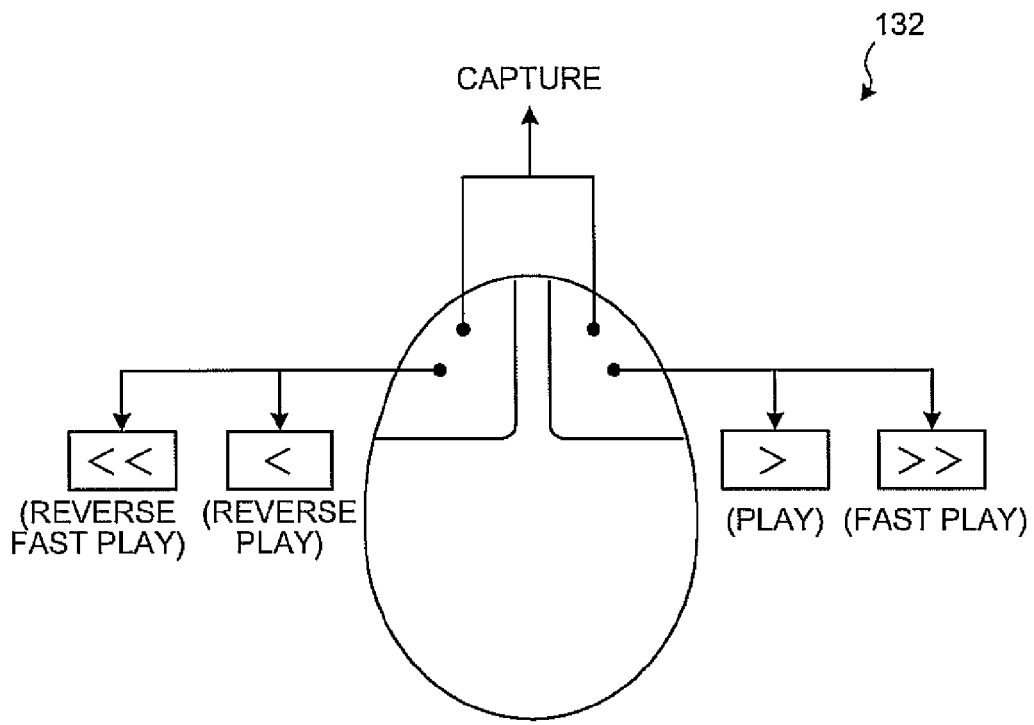
FIG. 4 is a schematic view schematically showing one example of a guidance image.
Figure 5:
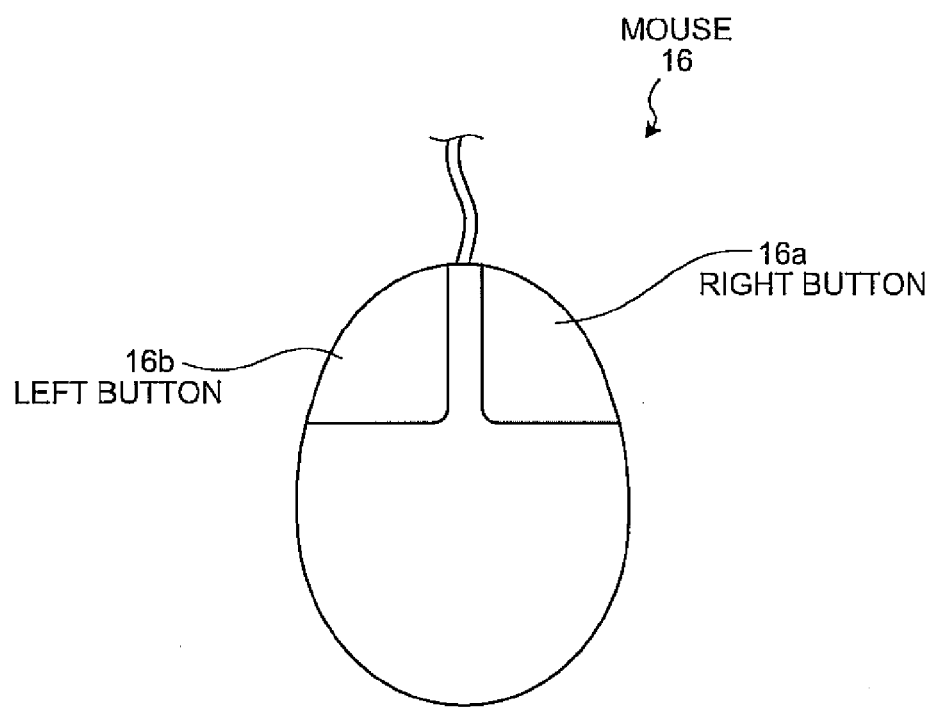
FIG. 5 is a schematic view schematically showing a mouse constituting an input unit.

FIG. 4 is a schematic view schematically showing one specific example of the guidance image 132. FIG. 5 is a schematic view schematically illustrating the mouse constituting the input unit 11. Notably, FIG. 4 illustrates the guidance image displayed in the pause state. As shown in FIG. 4, the guidance image 132 explains the button operation of the input unit 11 for changing the image display operation state in the button operation mode. Specifically, when the mouse is selected by the above-mentioned user setting, the guidance image 132 explains the button operation of the mouse 16 illustrated in FIG. 5.

Specifically, as shown in FIGS. 4 and 5, the guidance image 132 indicates that, if a button operation (right click operation) in which the right button 16a of the mouse 16 is depressed once is performed in the pause state, the mode is shifted from the pause state to the play state, and if a button operation (right double-click operation) in which the right button 16a is depressed twice in quick succession, the mode is shifted from the pause state to the fast play state. Further, the guidance image 132 indicates that, if a button operation (left click operation) in which the left button 16b of the mouse 16 is depressed once is performed in the current pause state, the mode is shifted from the pause state to the reverse fast play state, and if a button operation (left double-click operation) in which the left button 16b is depressed twice in quick succession, the mode is shifted from the pause state to the reverse fast play state. Moreover, the guidance image 132 indicates that, if a button operation (simultaneous click operation) in which the right button 16a and the left button 16b of the mouse 16 are both depressed is performed in the current pause state, the thumbnail corresponding to the observation image now being displayed in the main-image display area 100 is additionally displayed in the subimage display area 110. In the guidance image 132, "Capture", for example, is displayed as a text or mark indicating that the process for additionally displaying the thumbnail is performed.

Figure 6:
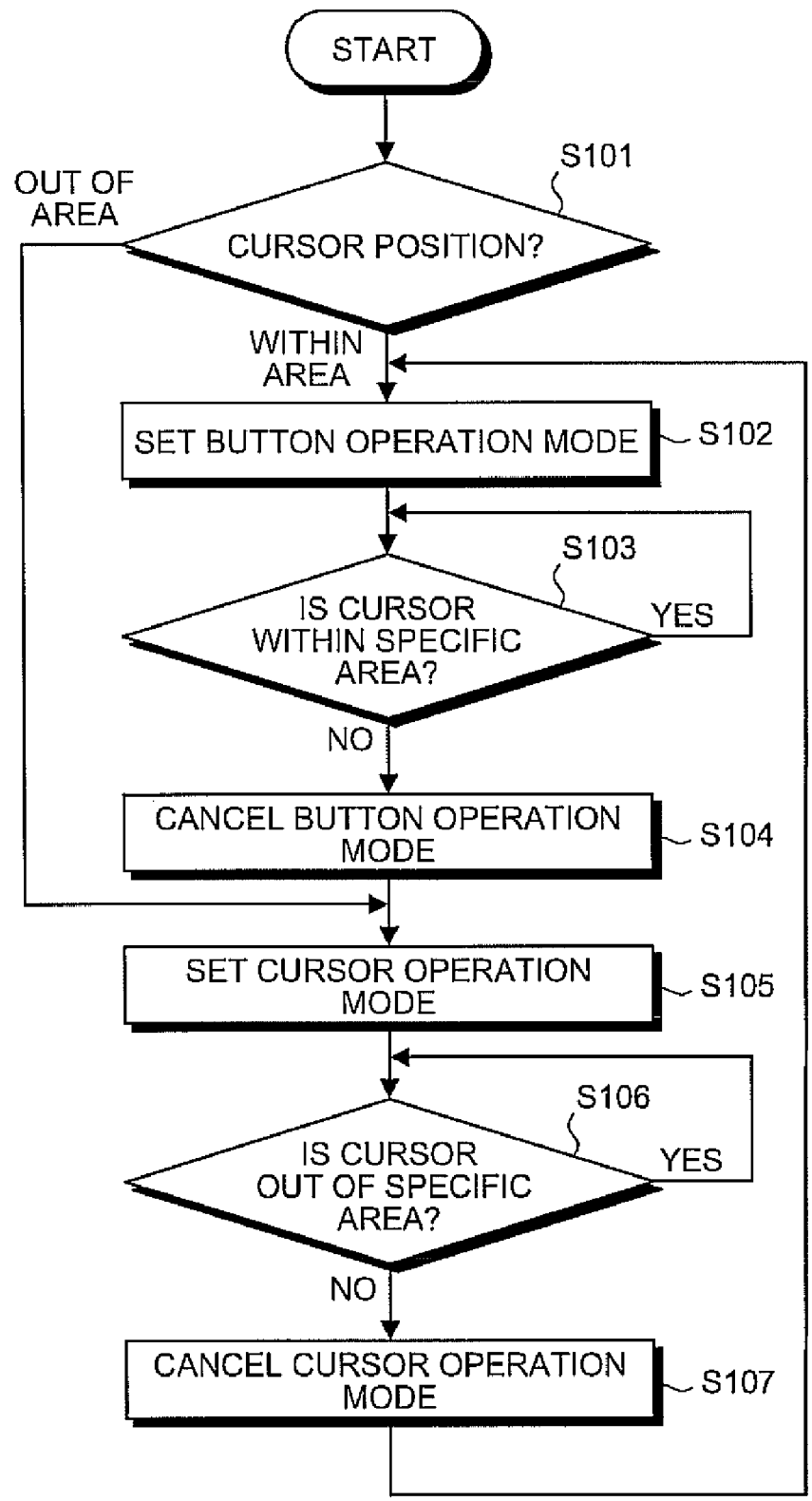
FIG. 6 is a flowchart for explaining a procedure for switching a display operation mode of an image according to a position of a cursor.

Next, the operation of the control unit 15 for changing the image display operation mode according to the position of the cursor K will be explained in detail. FIG. 6 is a flowchart for explaining a procedure of changing the image display operation mode according to the position of the cursor K. In FIG. 6, the control unit 15 firstly detects the position of the cursor K formed on the display screen of the display unit 12, and determines which position, at the inside of the frame of the specific area 130 or outside of the frame of the specific area 130, the cursor K is located (step S101).

When the control unit 15 determines that the position of the cursor K is at the inside of the frame of the specific area 130 at step S101 (in the area at step S101), the control unit 15 sets, for example, the above-mentioned button operation mode as the display operation mode for displaying the observation image of the inside of the subject 1 on the display unit 12 (step S102). In this case, if the display operation mode is set to the cursor operation mode before step S102, the mode switching controller 15a changes this cursor operation mode to the button operation mode with the movement of the cursor K to the inside of the frame of the specific area 130 defined as a trigger.

Next, the control unit 15 determines whether the cursor K is positioned in the frame of the specific area 130 or not (step S103). When the control unit 15 determines that the cursor K is positioned in the frame of the specific area 130 (Yes at step S103), the control unit 15 keeps the display operation mode to the button operation mode, and repeats this step S103.

On the other hand, when the control unit 15 determines at step S103 that the position of the cursor K is out of the frame of the specific area 130 (No at step S103), the control unit 15 cancels the button operation mode set at step S102 (step S104), and then, sets the cursor operation mode as the display operation mode (step S105). In this case, the mode switching controller 15a changes the display operation mode to the cursor operation mode from the button operation mode with the movement of the cursor K to the outside of the frame of the specific area 130 defined as a trigger.

Then, the control unit 15 determines whether the cursor K is positioned out of the frame of the specific area 130 or not (step S106). When the control unit 15 determines that the position of the cursor K is out of the frame of the specific area 130 (Yes at step S106), the control unit 15 maintains the display operation mode to the cursor operation mode, and repeats the step S106.

Thereafter, when the control unit 15 determines at the step S106 that the position of the cursor K is in the frame of the specific area 130 (No at step S106), the control unit 15 cancels the cursor operation mode set at the step S105 (step S107), and repeats the procedure after the step S102. In this case, the mode switching controller 15a changes the display operation mode from the cursor operation mode to the button operation mode with the movement of the cursor K to the inside of the frame of the specific area 130 defined as a trigger.

On the other hand, when the control unit 15 determines that the position of the cursor K is out of the frame of the specific area 130 at the aforesaid step S101 (out of area at step S101), the control unit 15 repeats the procedure after the step S105. In this case, the mode switching controller 15a changes the button operation mode to the cursor operation mode with the movement of the cursor K to the outside of the frame of the specific area 130 defined as a trigger, if the display operation mode is set to the button operation mode before the step S105.

As described above, when the position of the cursor K is in the frame of the specific area 130, the control unit 15 changes the display operation mode to the button operation mode and maintains this mode. When the position of the cursor K is out of the frame of the specific area 130, the control unit 15 changes the display operation mode to the cursor operation mode and maintains this mode. Accordingly, the examiner can designate any one of the display operation icons 121 to 127 so as to perform the display operation of the observation image by operating the input unit 11 to move the cursor K to the outside of the frame of the specific area 130, e.g., to the display operation icons 121 to 127. Further, if the examiner operates the input unit 11 to move the cursor K to the inside of the frame of the specific area 130, the examiner can carry out the button operation of the input unit 11, e.g., of the mouse 16 so as to perform the display operation of the observation image without moving the cursor K to the display operation icons 121 to 127.

Since the specific area 130 is formed sufficiently larger than the cursor K as shown in FIG. 3, go-in and go-out of the cursor K to the specific area 130 is easy, and further, an allowable range of the movement of the cursor K in the frame is large. Therefore, the examiner can easily move the cursor K to the inside of the frame of the specific area 130 by operating the input unit 11, e.g., the mouse 16, and even if the mouse 16 is shifted slightly, the examiner can keep the cursor K in the frame of the specific area 130. If the cursor K is positioned in the frame of the specific area 130, the control unit 15 maintains the aforesaid button operation mode regardless of the movement of the cursor K in the frame. Accordingly, the troublesome operation of moving the cursor K to the position of the display operation icon can be eliminated when performing the aforesaid display operation of the observation image, and further, the display operation in the button operation mode can easily be performed.

Figure 7:
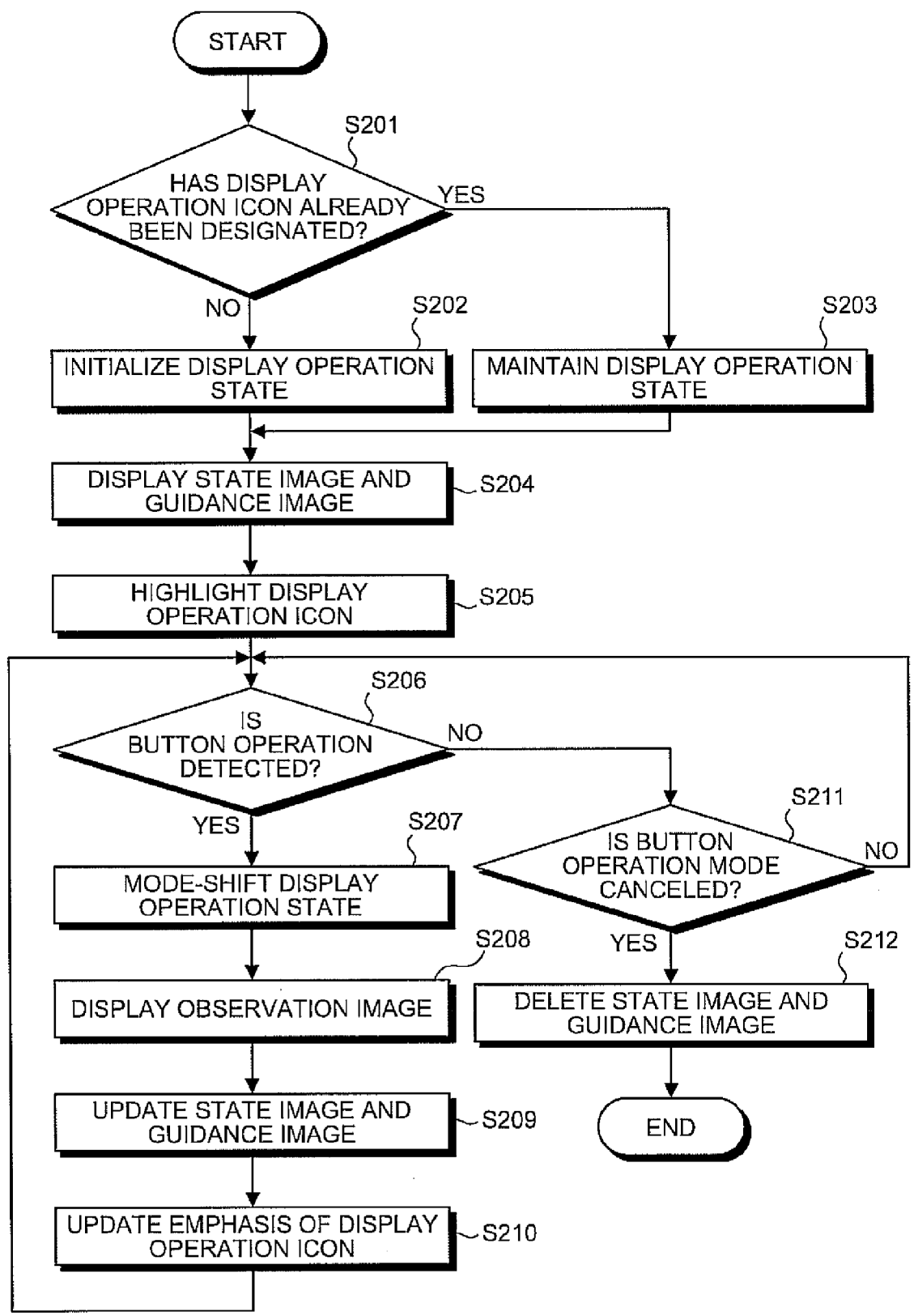
FIG. 7 is a flowchart for explaining a procedure of displaying an observation image by switching a display operation state in a button operation mode.

Next, the operation in which the control unit 15 sets the display operation state in the button operation mode and the observation image is displayed on the display unit 12 with this display operation mode will be explained in detail. FIG. 7 is a flowchart for explaining the procedure for displaying the observation image as the display operation state is changed in the button operation mode. In FIG. 7, when the control unit 15 sets the button operation mode as the display operation mode, the control unit 15 firstly determines whether or not any one of the display operation icons 121 to 127 has already been designated (step S201).

If none of the display operation icons 121 to 127 is designated by the operation of the input unit 11, the control unit 15 determines at step S201 that the display operation icons are not in their designated state (No at step S201), so that the control unit 15 initializes the display operation state of the observation image (step S202). In this case, the mode switching controller 15a sets, for example, the above-mentioned pause state as the initial setting of the display operation state. According to the initial setting of the mode switching controller 15a, the display controller 15b performs to the display unit 12 a control for displaying the observation image in the main-image display area 100 with the pause state.

Subsequently, the control unit 15 causes the display unit 12 to display the guidance image and the state image with the display operation state in the initial setting, e.g., with the pause state (step S204). In this case, the display controller 15b performs a control to display the state image 131 indicating the pause state and the guidance image 132 in the pause state in the specific area 130 as shown in FIG. 3.

Thereafter, the control unit 15 causes the display unit 12 to highlight the display operation icon, which designates the display operation state same as the state image displayed at the step S204 (step S205). In this case, the display controller 15b performs to the display unit 12 a control to highlight the display operation icon that designates the display operation state indicated by the state image. For example, when the display controller 15b performs a control to display the state image 131 in the specific area 130 at the step S204, for example, the display controller 15b performs a control to highlight the display operation icon 121 that designates the display operation state (i.e., pause state) same as the state image 131 as shown in FIG. 3.

On the other hand, if any one of the display operation icons 121 to 127 is designated by moving the cursor K and performing the click operation at the step S201, the control unit 15 determines that the display operation icon has already been designated (Yes at step S201), and maintains the display operation state corresponding to the designated display operation icon (step S203). In this case, the mode switching controller 15a sets the display operation state corresponding to the designated display operation icon of the display operation icons 121 to 127. The display controller 15b performs to the display unit 12 a control to display the observation image in the main-image display area 100 with the display operation state maintained at the step S203.

For example, if the display operation icon 121 has been designated, the mode switching controller 15a sets the pause state corresponding to this display operation icon 121. In this case, the display controller 15b performs a control to display the observation image in the main-image display area 100 with the set pause state. Further, if the display operation icon 123 has been designated, the mode switching controller 15a sets the play state corresponding to this display operation icon 123. In this case, the display controller 15b performs a control to display the observation image in the main-image display area 100 with the play state. Even if any one of the display operation icons 121 to 127 has been already designated, the mode switching controller 15a and the display controller 15b execute the process described above in the generally same manner as described above.

On the other hand, when the procedure up to the step S205 is executed, the control unit 15 detects the button operation of the input unit 11, e.g., the button operation of the mouse 16 (step S206). Specifically, when the button operation of the mouse 16 is performed with the position of the cursor K maintained in the frame of the specific area 130 at step S206, the control unit 15 detects the button operation of the mouse 16 (Yes at step S206), so that the control unit 15 mode-shifts the display operation state so as to correspond to the detected button operation (step S207). In this case, the mode switching controller 15a changes the display operation state (e.g., display operation state of the initial setting) maintained by the execution of this step S206 to the next display operation state corresponding to the button operation. With this operation, the mode switching controller 15a mode-shifts the display operation state to the next display operation state.

Next, the control unit 15 causes the display unit 12 to display the observation image with the next display operation mode that is shifted at step S207 (step S208). In this case, the display controller 15*b* performs to the display unit 12 a control to display the observation image in the main-image display area 100 with the next display operation state. By virtue of this operation, the display unit 12 displays the observation image in the display operation state before the mode-shift (e.g., the pause state) in the next display operation state (e.g., play state). Specifically, by this mode-shift, the display unit 12 sequentially plays the observation image that has been paused.

Thereafter, the control unit 15 updates the guidance image and the state image displayed on the display unit 12 to the guidance image and the state image in the next display operation state (step S209). In this case, the display controller 15*b* performs a control to update the state image indicating the display operation state before the mode-shift maintained at the step S206 to the state image indicating the next display operation state for display after the mode-shift at the step S207. At the same time, the display controller 15*b* performs a control to update the guidance image in the display operation state before the mode-shift to the guidance image in the next display operation state for display.

Then, the control unit 15 updates the highlighted display of the display operation icon so as to highlight the display operation icon designating the display operation state same as that of the state image updated at the step S209 (step S210). In this case, the display controller 15*b* performs to the display unit 12 a control to highlight the display operation icon designating the display operation state (i.e., the display operation state after the mode-shift at the step S207) indicated by the state image updated at the step S209, instead of highlighting the display operation icon corresponding to the display operation state before the mode-shift. Thereafter, the control unit 15 repeats the procedure after the step S206.

On the other hand, when the control unit 15 does not detect the button operation of the mouse 16 at the step S206 (No at step S206), the control unit 15 determines whether the button operation mode is canceled or not (step S211). When the control unit 15 determines that the position of the cursor K is out of the frame of the specific area 130 as described above, the control unit 15 cancels the button operation mode. When the control unit 15 determines that the position of the cursor K is out of the frame of the specific area 130, the control unit 15 maintains this button operation mode. When the control unit 15 determines that the button operation mode is not canceled at step S211 (i.e., that the button operation mode is maintained) (No at step S211), the control unit 15 repeats the procedure after this step S206.

When the control unit 15 determines that the button operation mode is canceled at step S211 (Yes at step S211), the control unit 15 deletes the state image and guidance image displayed in the specific area 130 (step S212), so as to complete the operation for displaying the observation image in this button operation mode. In this case, the display controller 15*b* performs to the display unit 12 a control to delete the state image and the guidance image now being displayed in the specific area 130.

Figure 8:
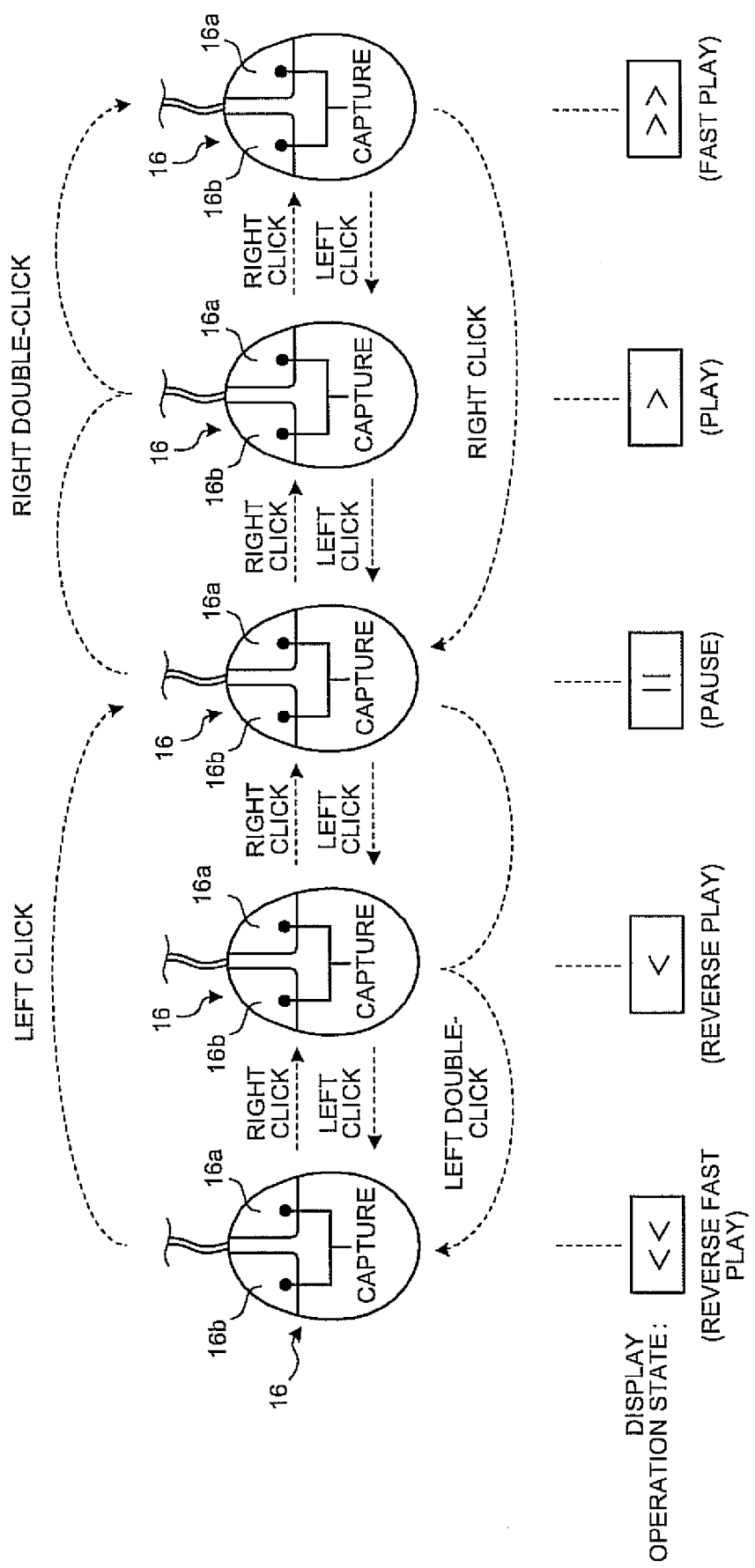
FIG. 8 is a state transition diagram for explaining an operation of shifting a mode of the display operation state of the observation image according to the button operation of the mouse.

Next, the operation of the mode-shift of the display operation state of the observation image in the aforesaid button operation mode will be explained in detail. FIG. 8 is a state transition diagram for explaining the operation of the mode-shift of the display operation state of the observation image according to the button operation of the mouse 16. The control unit 15 repeatedly executes the procedure after the step S201 to perform a mode-shift of the display operation state of the observation image every button operation of the mouse 16, and causes the display unit 12 to display the observation image in the display operation state set by the above-mentioned operation. In this case, the mode switching controller 15*a* shifts the display operation state before the mode-shift to the next display operation state every button operation of the mouse 16.

Specifically, in FIG. 8, when the display operation state before the mode-shift is, for example, the pause state, the mode switching controller 15*a* mode-shifts the pause state to the next display operation state, i.e., to the play state, if the mode switching controller 15*a* detects the right click operation of the mouse 16. If detecting the right double-click operation of the mouse 16 in the pause state, the mode switching controller 15*a* mode-shifts this pause state to the fast play state. If detecting the left click operation of the mouse 16 in the pause state, the mode switching controller 15*a* mode-shifts the pause state to the reverse play state. If detecting the left double-click operation of the mouse 16 in the pause state, the mode switching controller 15*a* mode-shifts the pause state to the reverse fast play state.

Similarly, if detecting the right click operation or right double-click operation of the mouse 16 in the play state, the mode switching controller 15*a* mode-shifts this play state to the fast play state or pause state, respectively. If detecting the left click operation or left double-click operation of the mouse 16 in the play state, the mode switching controller 15*a* mode-shifts this play state to the pause state or reverse play state, respectively. If detecting the right click operation or right double-click operation of the mouse 16 in the fast play state, the mode switching controller 15*a* mode-shifts this fast play state to the pause state or play state, respectively. If detecting the left click operation or left double-click operation of the mouse 16 in the fast play state, the mode switching controller 15*a* mode-shifts this fast play state to the play state or pause state, respectively.

Further, if detecting the right click operation or right double-click operation of the mouse 16 in the reverse play state, the mode switching controller 15*a* mode-shifts this reverse play state to the pause state or play state, respectively. If detecting the left click operation or left double-click operation of the mouse 16 in the reverse play state, the mode switching controller 15*a* mode-shifts this reverse play state to the reverse fast play state or pause state, respectively. Further, if detecting the right click operation or right double-click operation of the mouse 16 in the reverse fast play state, the mode switching controller 15*a* mode-shifts this reverse fast play state to the reverse play state or pause state, respectively. If detecting the left click operation or left double-click operation of the mouse 16 in the reverse fast play state, the mode switching controller 15*a* mode-shifts this reverse fast play state to the pause state or reverse play state, respectively.

If the control unit 15 detects the simultaneous click operation of the mouse 16 even in any one of the above-mentioned display operation states, the control unit 15 causes the display unit 12 to additionally display the thumbnail corresponding to the observation image being displayed on the main-image display area 100. In this case, the display controller 15*b* performs to the display unit 12 a control to additionally display the thumbnail in the subimage display area 110.

When the examiner performs a frame play or reverse frame play of the observation image, the examiner may operate the input unit 11 so as to make the display operation state in the pause state, and may operate the input unit 11 to select the display operation icon 122 or the display operation icon 125. In this case, each time the display controller 15*b* detects the button operation of the input unit 11 for selecting the display operation icon 122, the display controller 15*b* sequentially performs to the display unit 12 a control to display the observation image in the frame play state. Each time the display controller 15b detects the button operation of the input unit 11 for selecting the display operation icon 125, the display controller 15b sequentially performs to the display unit 12 a control to display the observation image in the reverse frame play state.

In order to execute the mode-shift process of the display operation state described above, the control unit 15 allocates each of the display operation states described below to the input unit 11, e.g., each button operation of the mouse 16, for every display operation state. In this case, the control unit 15 preferentially allocates the display operation state having high priority (e.g., the display operation state that has higher setting frequency compared to the other display operation states) as the next display operation state set by the mode-shift of the display operation state. Specifically, the control unit 15 preferentially allocates the play state and reverse play state, which are more frequently set compared to the other ones, to the right click operation and left click operation as the display operation state set next to the pause state, and preferentially allocates the fast play state and the reverse fast play state, which has the second highest setting frequency, to the right double-click operation and left double-click, operation by the mouse 16. In this case, since the right click operation and left click operation of the mouse 16 are easier button operation than the right double-click operation and the left double-click operation, the button operation for mode-shifting the pause state to the play state or reverse play state, which has high priority, is facilitated by allocating the display operation state to the button operation of the mouse 16.

Similarly to the above-mentioned case, the control unit 15 preferentially allocates the fast play state and pause state to the right click operation and left click operation of the mouse 16 respectively in the play state, and allocates the pause state and reverse play state to the right double-click operation and left double-click operation of the mouse 16 respectively in the play state. Further, the control unit 15 preferentially allocates the pause state and play state to the right click operation and left click operation of the mouse 16 respectively in the fast play state, and allocates the play state and pause state to the right double-click operation and left double-click operation of the mouse 16 respectively in the fast play state.

Further, the control unit 15 preferentially allocates the pause state and reverse fast play state to the right click operation and left click operation of the mouse 16 respectively in the reverse play state, and allocates the play state and pause state to the right double-click operation and left double-click operation of the mouse 16 respectively in the reverse play state. Further, the control unit 15 preferentially allocates the reverse play state and pause state to the right click operation and left click operation of the mouse 16 respectively in the reverse fast play state, and allocates the pause state and reverse play state to the right double-click operation and left double-click operation of the mouse 16 respectively in the reverse fast play state.

Every time the mode-shift of the display operation state is performed for every button operation of the mouse 16, for example, the control unit 15 updates the next display operation state, which is allocated to each button operation of the mouse 16, such that the button operation agrees with the allocation result of the next display operation state. Specifically, when the mode-shift is executed from the pause state to the play state, for example, the control unit 15 updates the play state that is allocated to the right click operation of the mouse 16 in the pause state to the fast play state, updates the reverse play state that is allocated to the left click operation to the pause state, updates the fast play state that is allocated to the right double-click operation to the pause state, and updates the reverse fast play state that is allocated to the left double-click operation to the reverse play state.

Figure 9:
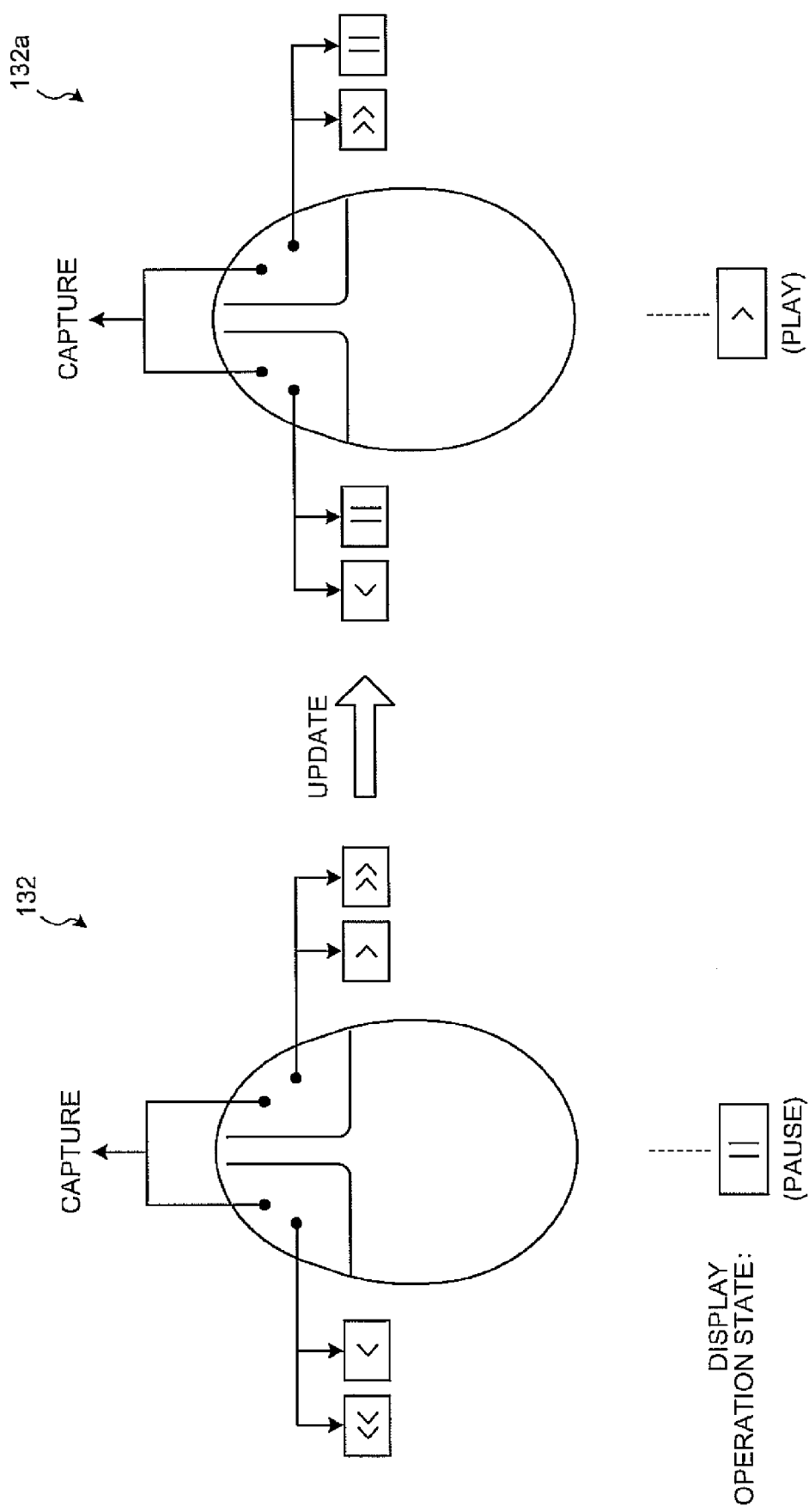
FIG. 9 is a schematic view for explaining one example of an operation for updating a guidance image.

Subsequently, the operation for updating the guidance image for every mode-shift of the display operation state will be explained in detail. FIG. 9 is a schematic view for explaining one example of the operation for updating the guidance image. Every time the control unit 15 performs the mode-shift of the display operation state as described above, it updates the guidance image that is being displayed on the display unit 12. In this case, the display controller 15b performs a control to update the guidance image that explains the button operation of the input unit 11 for shifting the mode of the display operation state to the next mode of the display operation state.

When the control unit performs a mode-shift of the display operation state to the play state from the pause state, for example, the display controller 15b performs a control to update the guidance image 132 in the above-mentioned pause state to a guidance image 132a in the play state as shown in FIG. 9. This guidance image 132a is for explaining each button operation of the mouse 16 in order to mode-shift the play state to the next display operation state. It indicates that the mode is shifted to the fast play state by the right click operation, the mode is shifted to the pause state by the left click operation or right double-click operation, and the mode is shifted to the reverse play state by the left double-click operation. Further, the guidance image 132a indicates that the thumbnail corresponding to the observation image is additionally displayed on the subimage display area 110 by the simultaneous click operation of the mouse 16.

The guidance image 132 explains each of the button operations of the mouse 16, which is allocated by the control unit 15 to each button so as to shift the mode of the display operation state in the pause state. The guidance image 132a explains each of the button operations of the mouse 16, which is allocated by the control unit 15 to each button so as to shift the mode of the display operation state in the play state. Specifically, the display controller 15b performs a control to update the guidance image so as to agree with the result of the allocation of the next display operation state to the aforesaid each button operation. Specifically, when the mode is shifted to the pause state, the display controller 15b performs a control to update the guidance image to the guidance image 132 in the form that agrees with the result of the allocation of each display operation state in the pause state. On the other hand, when the mode is shifted to the play state, the display controller 15b performs a control to update the guidance image to the guidance image 132a in the form that agrees with the result of the allocation of each display operation state in the play state. Further, when the mode is shifted to the fast play state, the display controller 15b performs a control to update the guidance image to a guidance image in the form that agrees with the result of the allocation of each display operation state in the fast play state. When the mode is shifted to the reverse play state, the display controller 15b performs a control to update the guidance image to a guidance image that agrees with the result of the allocation of each display operation state in the reverse play state, while when the mode is shifted to the reverse fast play state, the display controller 15b performs a control to update the guidance image to a guidance image in the form that agrees with the result of the allocation of each display operation state in the reverse fast play state.

Further, the guidance image 132 explains each button operation for performing the mode-shift to the play state having higher setting frequency, reverse play state, fast play state, and reverse fast play state, as the display operation state subsequent to the pause state. The guidance image 132a explains each button operation for performing the mode-shift to the fast play state having higher frequency, pause state, and reverse play state, as the display operation state subsequent to the play state. Specifically, as illustrated in the guidance images 132 and 132a, the guidance image for every display operation state preferentially explains the button operation for shifting the display operation state to the mode having higher priority (e.g., having higher setting frequency), as the display operation state subsequent to the display operation state.

Figure 10:
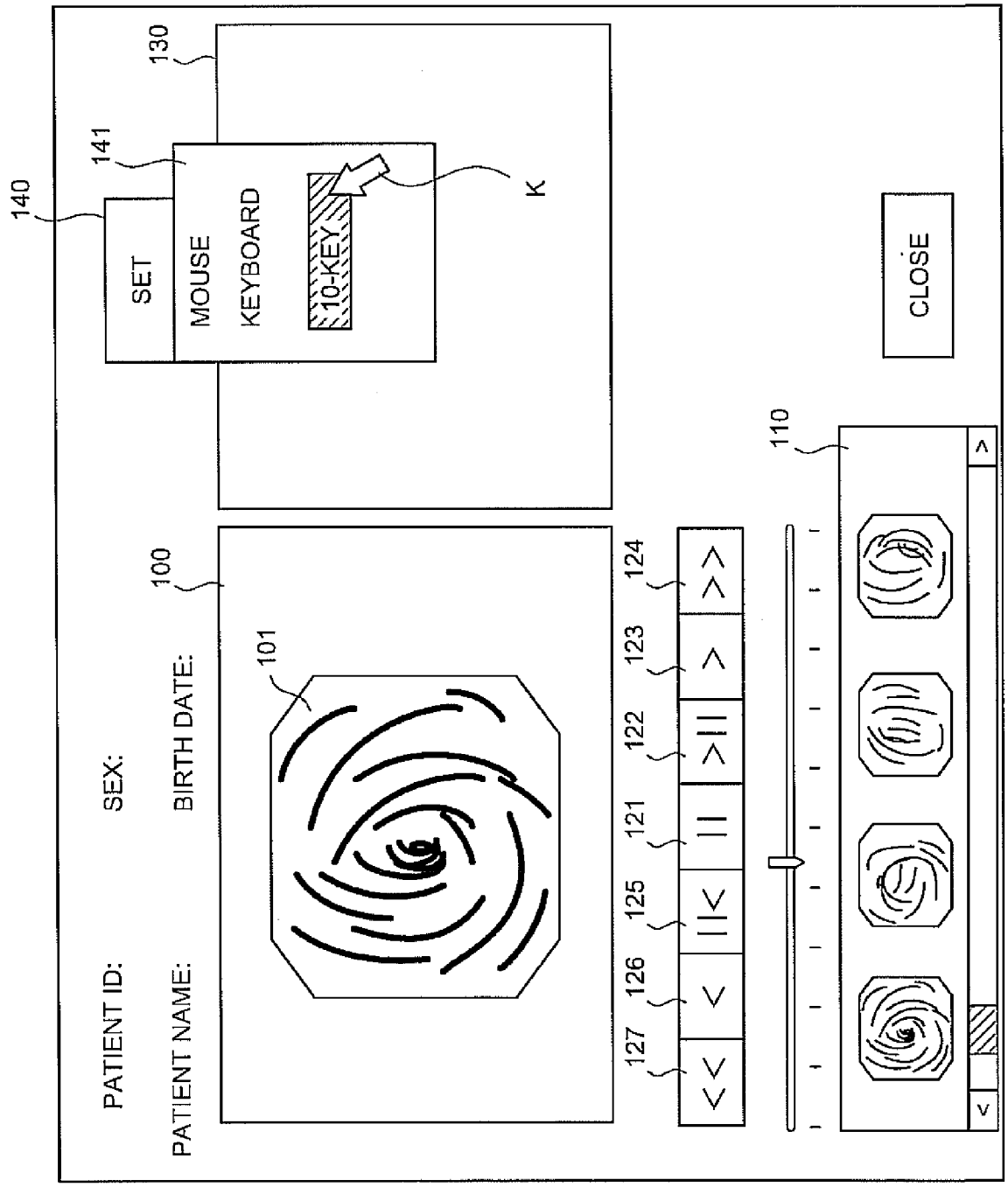
FIG. 10 is a schematic view schematically showing one specific example of a display screen when a user setting for selecting an input unit is performed.

Next, the user setting for selecting the input unit 11 in order to perform the display operation of the observation image will be explained. FIG. 10 is a schematic view schematically showing one specific example of the display screen in the event that the user setting for selecting the input unit 11 is performed. When the examiner operates the input unit 11 to perform a click operation with the cursor K positioned on the setting icon 140 so as to designate the setting icon 140, a select window 141 is opened as shown in FIG. 10. The select window 141 displays a device of the input unit 11, which is the subject to be selected, for performing the display operation of the observation image, such as a mouse, keyboard, and ten-key (10-key). If the examiner moves the cursor K to designate a desired device among the devices, which are the subjects to be selected, displayed on the select window 141, the examiner can select the device of the input unit 11 for performing the display operation of the observation image. In this case, the control unit 15 allocates each of the display operation states to the selected device.

For example, when the mouse is selected from the select window 141, the control unit 15 allocates each of the display operation states to the button operation of the mouse 16 as described above. In this case, the display controller 15b causes the display unit 12 to display the guidance image (e.g., guidance image 132) for explaining each of the button operations of the mouse 16 in order to perform the mode-shift of the display operation state as described above.

On the other hand, when the ten-key is selected from the select window 141, the control unit 15 allocates each of the display operation states to each of the input buttons of the ten-key constituting the input unit 11. In this case, the control unit 15 allocates the desired display operation state and the next display operation state to the adjacent input buttons in the input button group provided to the ten-key of the input unit 11. Accordingly, the mode switching controller 15a performs a control to perform the mode-shift to the display operation state corresponding to the operated input button of the ten-key. The next display operation state described above is desirably the display operation state having higher priority (having higher setting frequency) than the other display operation states, as the display operation state shifted from the display operation state allocated to the adjacent input button.

Figure 11:
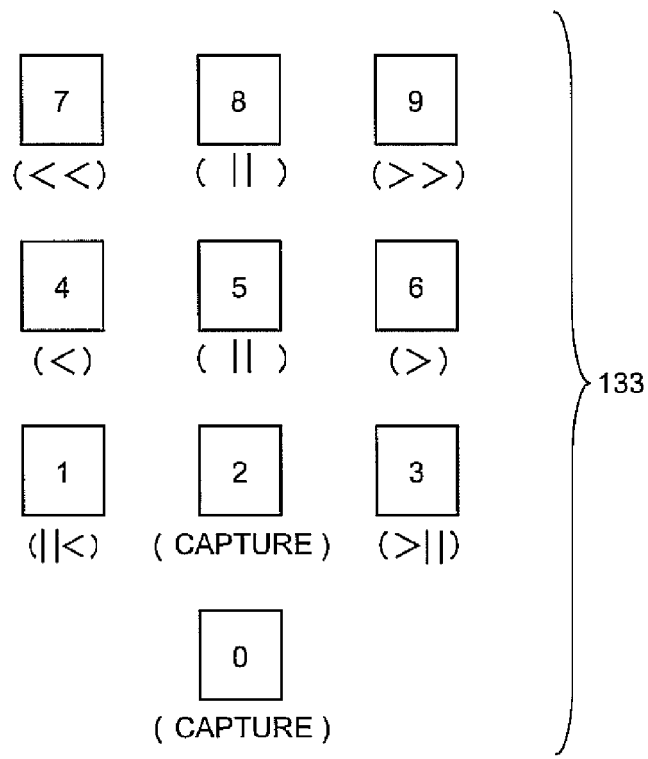
FIG. 11 is a schematic view schematically showing one example of a guidance image for explaining a button operation of a ten-key.

Further, the display controller 15b displays on the display unit 12 the guidance image for explaining each of the button operations of the ten-key in order to perform the mode-shift of the display operation state, instead of the guidance image corresponding to the mouse 16. FIG. 11 is a schematic view schematically showing one example of the guidance image for explaining the button operation of the ten-key in order to perform the mode-shift of the display operation state. The display controller 15b performs a control to display the guidance image 133 shown in FIG. 11, for example, instead of the guidance image 132.

The guidance image 133 explains the button operation of the ten-key for performing the mode-shift of the display operation state as shown in FIG. 11. In this case, the correspondence between each input button and each display operation state shown in the guidance image 133 agrees with the result of the allocation of each display operation state to each input button by the control unit 15. For example, in the guidance image 133, the input button for shifting the mode to the pause state and the input button for shifting the mode to the mode having higher priority (e.g., play state ">", fast play state ">>", reverse play state "<", reverse fast play state "<<", frame play state ">|", and reverse frame play state "|<") as the next display operation state are displayed adjacently to each other. Further, the guidance image 133 indicates that the thumbnail corresponding to the observation image is additionally displayed in the subimage display area 110 by the button operation of depressing once the remaining input buttons of the ten-key ("2" key and "0" key in FIG. 11).

When the ten-key is selected from the select window 141, each of the display operation states may be allocated to each input button of the ten-key unit provided at the keyboard constituting the input unit 11, like the aforesaid ten-key. In this case, the guidance image 133 explains the button operation of each button of the ten-key unit of the keyboard.

On the other hand, when the keyboard is selected from the select window 141, the control unit 15 allocates each display operation state to each input button of the keyboard constituting the input unit 11. In this case, the control unit 15 allocates a desired display operation state and the next display operation state to the input buttons, which are adjacent to each other, of the input button group provided to the keyboard of the input unit 11. Accordingly, the mode switching controller 15a performs a control to perform the mode-shift of the display operation state corresponding to the operated input button of the ten-key. It is desirable that the next display operation state is the display operation state that is shifted from the display operation state allocated to the adjacent input button and has higher priority (e.g., higher setting frequency) than the other states.

Figure 12:
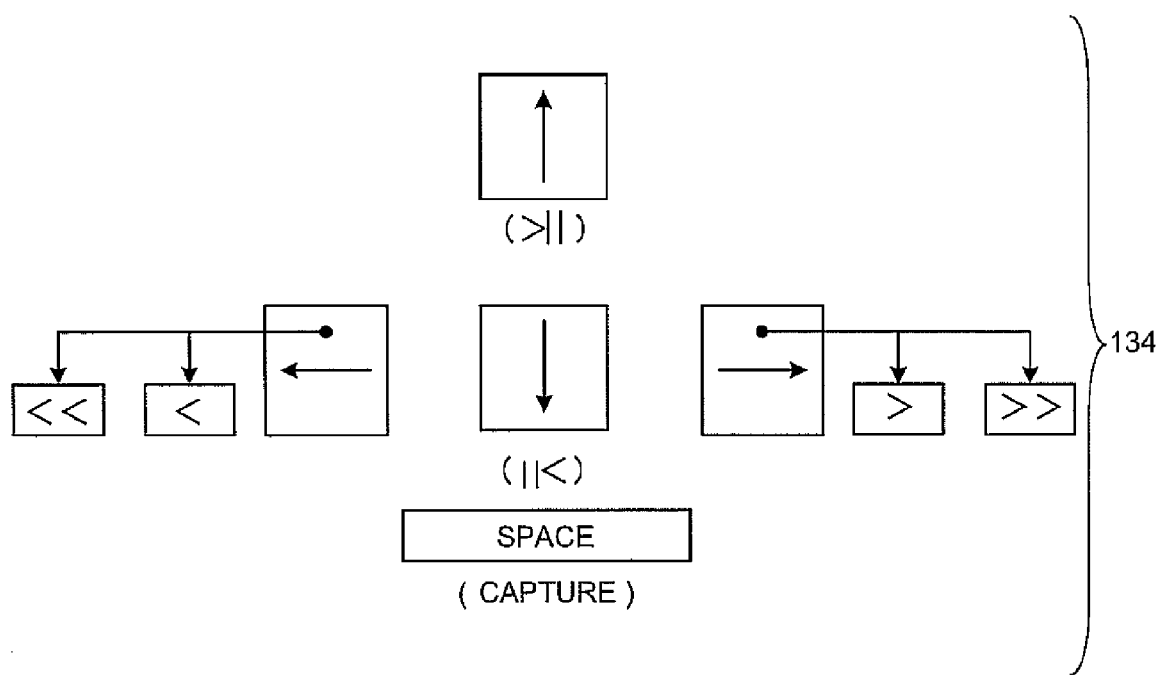
FIG. 12 is a schematic view schematically showing one example of a guidance image for explaining a button operation of a keyboard.

The display controller 15b causes the display unit 12 to display a guidance image for explaining the button operation of each button of the keyboard in order to perform the mode-shift of the display operation state, instead of the guidance image corresponding to the mouse 16. FIG. 12 is a schematic view for schematically showing one example of the guidance image for explaining the button operation of the keyboard to perform the mode-shift of the display operation state. The display controller 15b performs a control to display a guidance image 134 shown in FIG. 12, instead of the guidance image 132.

The guidance image 134 explains the button operation of each button of the keyboard so as to perform the mode-shift of the display operation state as shown in FIG. 12. In this case, the correspondence between each input button and each display operation state shown in the guidance image 134 agrees with the result of the allocation of each display operation state to each button by the control unit 15. For example, in the guidance image 134, with respect to the input button for shifting the mode to the frame play state (upward arrow key) and the input button for shifting the mode to the reverse frame play mode (downward arrow key), the input buttons (specifically, rightward arrow key and leftward arrow key) for shifting the mode to the mode having higher priority (e.g., play state ">", fast play state ">>", reverse play state "<", reverse fast play state "<<") are displayed adjacently to each other as the next display operation states. Moreover, the guidance image 134 indicates that the mode is shifted to the play state or reverse play state by the button operation of depressing once the rightward arrow key or by the button operation of depressing once the leftward arrow key, and the mode is shifted to the fast play state or reverse fast play state by the button operation of depressing the rightward arrow key continuously twice or by the button operation of depressing the leftward arrow key continuously twice. Further, the guidance image 134 indicates that the thumbnail corresponding to the observation image is additionally displayed in the subimage display area 110 by the button operation of depressing once a space key.

When the display operation state is mode-shifted for every button operation of the mouse of the input unit 11, the mode is shifted to the display operation state having higher priority as the display operation state subsequent to the display operation state before the mode-shift in the embodiment of the present invention. However, the present invention is not limited thereto. It may be configured such that the mode is shifted to the desired display operation state from the display operation state before the mode-shift for every button operation of the mouse at the input unit 11. As one example of this configuration, the apparatus may be configured such that the mode is shifted along the arrangement of the display operation icons 121 to 127, for example, for every button operation of the mouse. In this case, each of the display operation states may be allocated to the button operation of each button of the mouse in such a manner that the mode-shift is performed in a manner in which the frame play state is added between the pause state and the play state and the reverse frame play state is added between the pause state and the reverse play state in the state transition diagram shown in FIG. 8.

In the embodiment of the present invention, when the display operation state is mode-shifted for every button operation of the mouse 16, the mode is shifted to the frame play state or reverse frame play state by moving the cursor K to the display operation icons 122 and 125 in the pause state. However, the invention is not limited thereto. The apparatus may be configured such that the frame play state and reverse frame play state are allocated to the button operation of the mouse 16, and the mode is shifted to the frame play state or reverse frame play state by the button operation of the mouse 16. In this case, for example, it may be configured such that the mode is shifted to the frame play state by the right double-click operation of the mouse 16, and the mode is shifted to the reverse frame play state by the left double-click operation of the mouse 16 in the desired display operation state or all display operation states. Alternatively, it may be configured such that the mode is shifted to the frame play state by the button operation of depressing the right button 16a with the left button 16b depressed, and the mode is shifted to the reverse frame play state by the button operation of depressing the left button 16b with the right button 16a depressed.

Although the aforesaid state image and the guidance image are displayed in the frame of the specific area 130 in the embodiment of the present invention, the invention is not limited thereto. The state image and the guidance image may be displayed out of the frame of the specific area 130.

In the embodiment of the present invention, the state image is displayed, and the display operation icon corresponding to the display operation state indicated by the state image is highlighted. However, the invention is not limited thereto. At least either one of the display of the state image and the highlighted display of the display operation icon may be performed.

In the embodiment of the present invention, the state image indicating the mark of the display operation icon is displayed. However, the invention is not limited thereto. A text indicating the display operation state or the state image indicating a desired mark may be displayed. Alternatively, a state image in which the mark of the display operation icon and the text indicating the display operation state are combined may be displayed.

Figure 13:
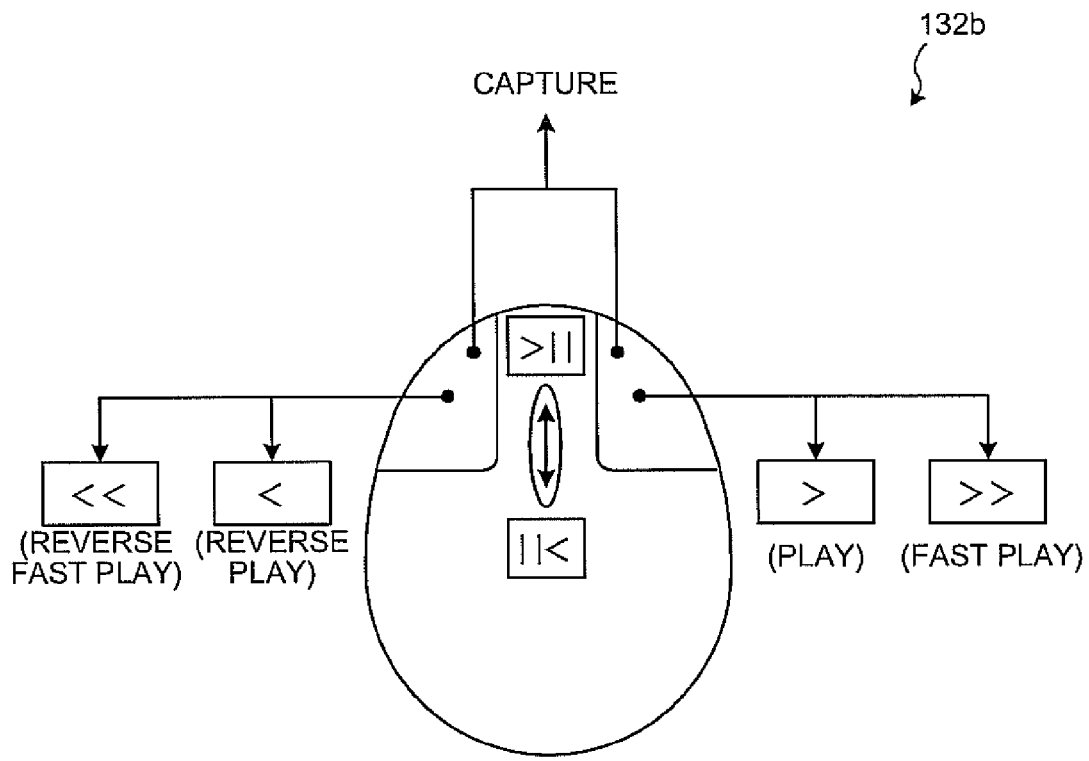
FIG. 13 is a schematic view schematically showing one example of a guidance image corresponding to a mouse provided with a scroll dial.
Figure 14:
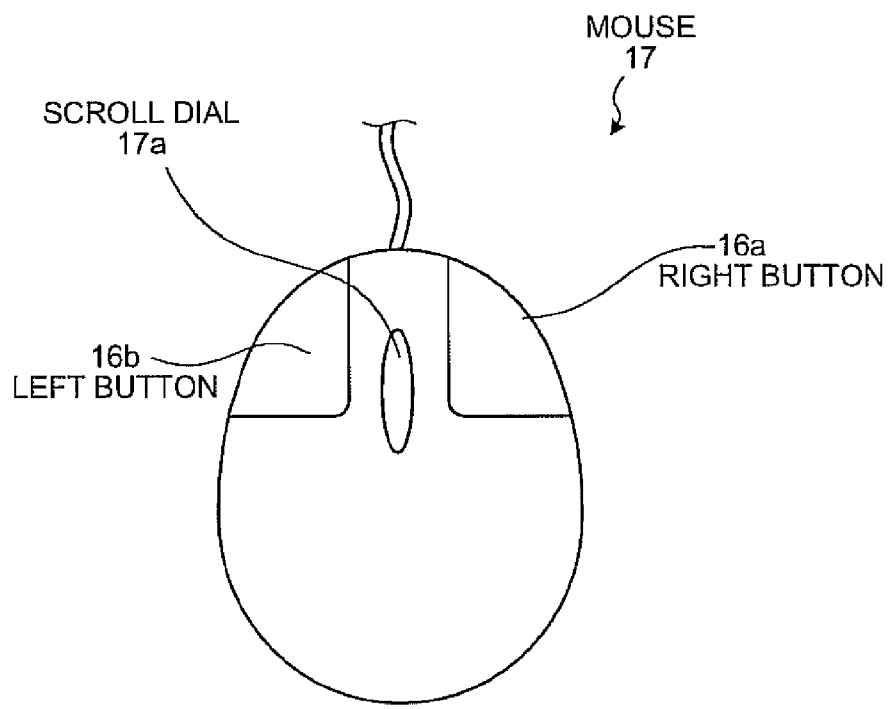
FIG. 14 is a schematic view schematically illustrating a mouse provided further with a scroll dial.

In the embodiment of the present invention, the mouse 16 is employed as a pointing device constituting the input unit 11. However, the invention is not limited thereto. Pointing devices of various forms, such as a mouse, trackball, touch pad, etc., may be employed. In this case, a mouse 17 provided with a scroll dial may be used instead of the mouse 16. FIG. 13 is a schematic view schematically showing one example of a guidance image corresponding to the mouse provided with the scroll dial. FIG. 14 is a schematic view schematically illustrating the mouse provided with the scroll dial. It is to be noted that FIG. 13 illustrates the guidance image displayed in the pause state.

As shown in FIGS. 13 and 14, the mouse 17 has a configuration in which the scroll dial 17a is further provided to the mouse 16. The guidance image 132b explains the mode-shift operation of the display operation state using the mouse 17. In this case, the guidance image 132b explains the button operation same as that of the aforesaid guidance image 132, i.e., the button operation of each button for shifting the mode from the pause state to the play state, reverse play state, fast play state, or reverse fast play state, and further explains the scroll dial operation for shifting the mode to the frame play state or reverse frame play state. Specifically, the guidance image 132b indicates that the mode is shifted to the frame play state when the scroll dial 17a is turned in the upward direction in FIG. 14, and indicates that the mode is shifted to the reverse frame play state when the scroll dial 17a is turned in the downward direction in FIG. 14. When the mouse 17 described above is used instead of the mouse 16, the control unit 15 allocates the frame play state and the reverse frame play state to each scroll dial operation of the mouse 17 respectively, and the display controller 15b may perform a control to display the guidance image 132b in the pause state instead of the guidance image 132.

As explained above, in the embodiment of the present invention, when a specific area formed to have a predetermined size is displayed, and a cursor on a display screen is within this specific area, a button operation mode for performing an image display operation with the button operation of the input unit such as a mouse or keyboard is set. When the cursor on the display screen is out of the specific area, a cursor operation mode for performing the image display operation corresponding to the position on the display screen (e.g., display operation icon) and the position of the cursor is set. Therefore, if the cursor is positioned within the specific area, the image display operation can be performed by the button operation of the input unit, regardless of the position of the cursor, whereby the invention provides an effect of realizing an image display apparatus that can easily perform the image display operation while observing a series of images of the inside of a subject on the display screen.

By using the image display apparatus according to the present invention, an examiner such as a doctor or nurse can easily perform the image display operation, while observing the series of images of the inside of the subject displayed on the display screen. Therefore, the oversight of the image, which is to be observed, displayed on the display screen can be prevented, and further, the display operation state of the image, such as the pause state, play state, etc., can easily be switched.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus comprising:
a display unit that displays a series of images obtained by imaging an inside of a subject in time sequence, and displays a specific area with a predetermined size;
an input unit having an input button group for performing a display operation of the images; and
a control unit configured to set an operation mode to a button operation mode for performing the display operation of the images with a button operation of the input unit when a cursor on a display screen is in the specific area, and configured to set the operation mode to a cursor operation mode for performing the display operation of the images corresponding to at least a position on the display screen and a position of the cursor when the cursor is out of the specific area;
wherein the control unit causes the display unit to display a guidance image for explaining a button operation of the input unit when the operation mode is set to the button operation mode.

2. The image display apparatus according to claim 1, wherein
the input unit includes a pointing device; and
the control unit performs a control to perform a mode-shift of the display operation state of the images to a next display operation state for every button operation of the pointing device in the button operation mode.

3. The image display apparatus according to claim 2, wherein
the control unit updates the next display operation state that is shifted by a next button operation of the pointing device, every time the display operation state of the images is mode-shifted.

4. The image display apparatus according to claim 2, wherein
the next display operation state has a priority, for being a display operation state after a mode-shift from the display operation state, higher than other display operation states.

5. The image display apparatus according to claim 2, wherein
the control unit controls the display unit so that a state image indicating the display operation state is displayed.

6. The image display apparatus according to claim 5, wherein
the display unit displays a plurality of display operation icons for designating the display operation state at a position on the display screen, and
the state image indicates a mark of one of the display operation icons.

7. The image display apparatus according to claim 6, wherein
the control unit controls the display unit so that one of the display operation icons is highlighted, the one of the display operation icons designating the same display operation state as the display operation state after the mode-shift.

8. The image display apparatus according to claim 1, wherein
the input unit includes a keyboard or a ten-key, and
the control unit performs a control to perform a mode-shift of the display operation state to a next display operation state for every button operation of the keyboard or ten-key in the button operation mode.

9. The image display apparatus according to claim 8, wherein
the control unit allocates the display operation of the images and the next display operation state to each of adjacent input buttons in the input button group of the keyboard or ten-key.

* * * * *